United States Patent
Wang

(10) Patent No.: US 10,941,219 B2
(45) Date of Patent: Mar. 9, 2021

(54) METHOD FOR REFINING SUGAMMADEX SODIUM

(71) Applicant: Hefei Bosike Pharmtech Co., Ltd., Hefei (CN)

(72) Inventor: Bingyong Wang, Nanjing (CN)

(73) Assignee: Hefei Bosike Pharmtech Co., Ltd., Hefei (CN)

( * ) Notice: Subject to any disclaimer, the term of this patent is extended or adjusted under 35 U.S.C. 154(b) by 153 days.

(21) Appl. No.: 16/320,492

(22) PCT Filed: Aug. 2, 2017

(86) PCT No.: PCT/CN2017/095642
§ 371 (c)(1),
(2) Date: Jan. 25, 2019

(87) PCT Pub. No.: WO2018/036353
PCT Pub. Date: Mar. 1, 2018

(65) Prior Publication Data
US 2020/0172635 A1   Jun. 4, 2020

(30) Foreign Application Priority Data
Aug. 24, 2016 (CN) .......................... 201610716744.2

(51) Int. Cl.
*C08B 37/16* (2006.01)
(52) U.S. Cl.
CPC ................................ *C08B 37/0012* (2013.01)
(58) Field of Classification Search
None
See application file for complete search history.

(56) References Cited

U.S. PATENT DOCUMENTS

| 6,670,340 B1 | 12/2003 | Zhang et al. |
| 2018/0251575 A1* | 9/2018 | Jia .................... C08B 37/0012 |

FOREIGN PATENT DOCUMENTS

| CN | 1402737 A | 3/2003 |
| CN | 104844732 A | 8/2015 |
| CN | 105273095 A | 1/2016 |
| CN | 105348412 A | 2/2016 |
| WO | 2012025937 A1 | 3/2012 |
| WO | 2014125501 A1 | 8/2014 |
| WO | 2017084401 A1 | 5/2017 |

OTHER PUBLICATIONS

Julia M. Adam et. al., Cyclodextrin-Derived Host Molecules as Reversal Agents for the Neuromuscular Blocker Rocuronium Bromide: Synthesis and Structure-Activity Relationships, J. Med. Chem., Mar. 21, 2002, p. 1806-1816, vol. 45, No. 9.
Hai Ming Wang et. al., Solubilization of Polycyclic Aromatics in Water by γ-Cyclodextrin Derivatives, Chem. Asian J., 2011, p. 2390-2399, 6.

* cited by examiner

*Primary Examiner* — Layla D Berry
(74) *Attorney, Agent, or Firm* — Bayramoglu Law Offices LLC

(57) ABSTRACT

A method for refining sugammadex sodium is provided: adding a protective agent to crude sugammadex sodium, and obtaining pure sugammadex sodium by performing recrystallization under the protection of inert gas. Among them, the protective agent is one or a mixture of two or more, in any ratio, selected from the group consisting of mercaptoethanol, thioglycolate, thioglycolate ester, mercaptopropionate, mercaptopropionate ester, glutathione, cysteine, cystamine, dithioerythritol, dithiothreitol, trisubstituted organophosphorus compound, and salt of the trisubstituted organophosphorus compound. The method is simple in operation, high in product purity, good in economy, and more suitable for industrial production.

5 Claims, 4 Drawing Sheets

Area Percentage Report

Sorted By          : Signal
Multiplier         :           1.0000
Dilution           :           1.0000
Use Multiplier & Dilution Factor with ISTDs Signal 1: VWD1 A, Wavelength=200 nm

| Peak # | Ret Time [min] | Type | Width [min] | Area [mAU*s] | Height [mAU] | Area % |
|---|---|---|---|---|---|---|
| 1 | 10.130 | BB | 0.3155 | 692.96118 | 30.67679 | 0.7896 |
| 2 | 13.050 | BB | 0.3552 | 827.31543 | 33.14454 | 0.9426 |
| 3 | 14.939 | BB | 0.3386 | 453.02847 | 19.82142 | 0.5162 |
| 4 | 18.347 | BB | 0.3843 | 44.70901 | 1.83444 | 0.0509 |
| 5 | 20.885 | BV | 0.4071 | 38.05326 | 1.52489 | 0.0434 |
| 6 | 21.974 | VB | 0.8970 | 8.54134e4 | 1446.24695 | 97.3193 |
| 7 | 25.910 | BB | 0.3953 | 88.64419 | 3.50217 | 0.1010 |
| 8 | 32.650 | BB | 0.4098 | 82.72910 | 3.11593 | 0.0943 |
| 9 | 36.257 | BB | 0.2699 | 18.88029 | 1.11304 | 0.0215 |
| 10 | 40.971 | BB | 0.4370 | 54.28815 | 1.92508 | 0.0619 |
| 11 | 50.202 | BB | 0.1490 | 17.69244 | 1.89299 | 0.0202 |
| 12 | 57.161 | BB | 0.1168 | 34.41608 | 4.73535 | 0.0392 |

Totals :                        8.77661e4    1549.53359

* Report End *

METHOD FOR REFINING SUGAMMADEX SODIUM

CROSS REFERENCE TO RELATED APPLICATIONS

This application is the national phase entry of International Application No. PCT/CN2017/095642, filed on Aug. 2, 2017, which is based upon and claims priority to Chinese Patent Application No. 201610716744.2, filed on Aug. 24, 2016, the entire contents of which are incorporated herein by reference.

TECHNICAL FIELD

The present invention relates to a method for refining sugammadex sodium, belonging to the technical field of medicine production.

BACKGROUND

Sugammadex sodium, chemically designated as 6A,6B,6C,6D,6E,7F,6G,6H-octakis-S-(2-carboxyethyl)-6A,6B,6C,6D,6E,7F,6G,6H-octathio-γ-cyclodextrin octasodium salt, has a structural formula as follows:

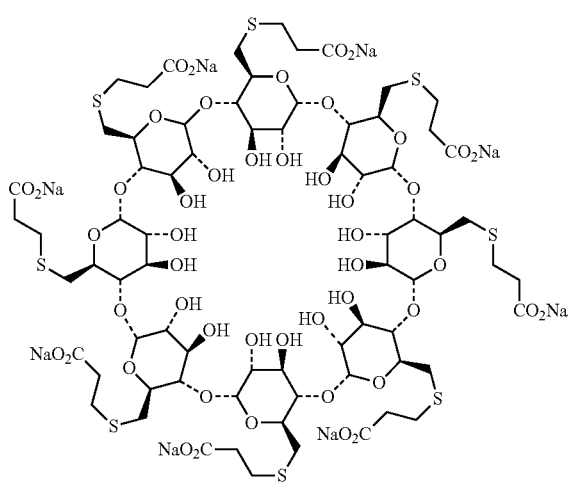

Sugammadex sodium is a novel muscle relaxant reversal agent developed by Organon Corp., the Netherlands. Sugammadex sodium is clinically used for reversal of neuromuscular blockade induced by rocuronium and vecuronium, showing good efficacy and excellent safety. Since sugammadex sodium is approved for listing by the European Union in July 2008, it has been marketed in Japan, South Korea, the United States and other countries, and is applying for production and marketing in China.

Sugammadex sodium is a structurally modified γ-cyclodextrin, the structure thereof is complicated, and a large number of complex by-products and degradation impurities are prone to be generated during the preparation process. Moreover, a thioether bond exists in the molecular structure of the sugammadex sodium, which causes the compound to be unstable to oxygen, and is easily oxidized during the purification process to form a series of impurities such as sulfoxide, sulfone, disulfide, etc. Most of the impurities are produced in the side chain structure of the sugammadex sodium molecule. The structures of the impurities are similar to that of the sugammadex sodium, with small polarity difference and small molecular weight difference, so it is difficult to remove the impurities by conventional means. This property makes it very difficult to purify the sugammadex sodium.

At present, there are few reports on the preparation process of sugammadex sodium at home and abroad. The purification process of the sugammadex sodium relies on membrane dialysis or column chromatography method, and it is difficult to obtain high-purity products, which is not conducive to large-scale industrial production.

J. Med. Chem. 2002, 45, 1806-1816PP proposed that in N,N-dimethylformamide system, under the catalysis of triphenylphosphorus, bromine reacted with γ-cyclodextrin to obtain 6-deoxy-6-perbromo-γ-cyclodextrin; then the 6-deoxy-6-perbromo-γ-cyclodextrin reacted with methyl 3-mercaptopropionate under the catalysis of anhydrous cesium carbonate to obtain the product, i.e., sugammadex methyl ester; the sugammadex methyl ester was then hydrolyzed by sodium hydroxide to obtain sugammadex sodium. The yield was 60%. The product obtained by this method was crude sugammadex sodium with low purity, no further refining and purification were reported.

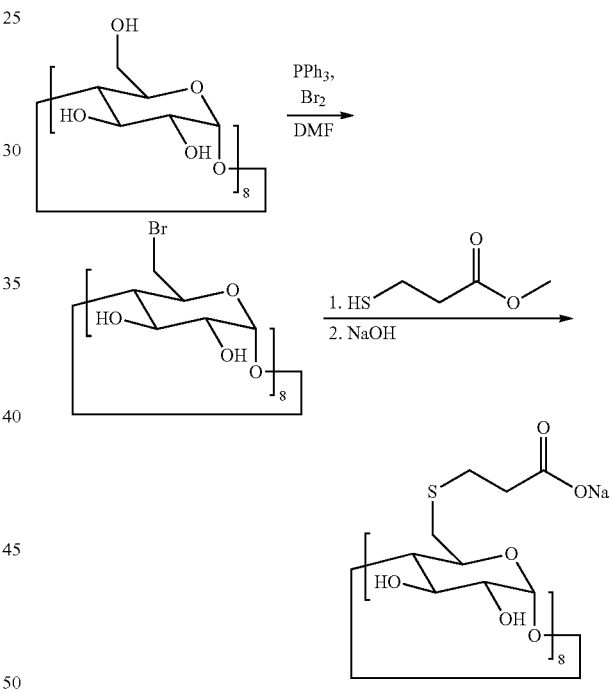

Chem. Asian J. 2011, 6, 2390-2399 reported that γ-cyclodextrin was first iodized to obtain crude 6-deoxy-6-periodo-γ-cyclodextrin; this crude product reacted with acetic anhydride to form ester, the ester was then purified by silica gel column chromatography and then hydrolyzed by sodium methoxide to obtain 6-deoxy-6-periodo-γ-cyclodextrin refined product with higher purity; the refined product was finally etherified with 3-mercaptopropionic acid to obtain the target product. During the reaction, the purity of the intermediate product is high, the impurities are few, and the post-treatment and purification of the product are relatively simple. However, the preparation of iodo-cyclodextrin by column chromatography has complicated the reaction step and is time-consuming. Moreover, when the iodo-cyclodextrin prepared by this method is used as a raw material to prepare the sugammadex sodium, the qualified product cannot be directly obtained, and the purification of sugammadex sodium products would still be difficult.

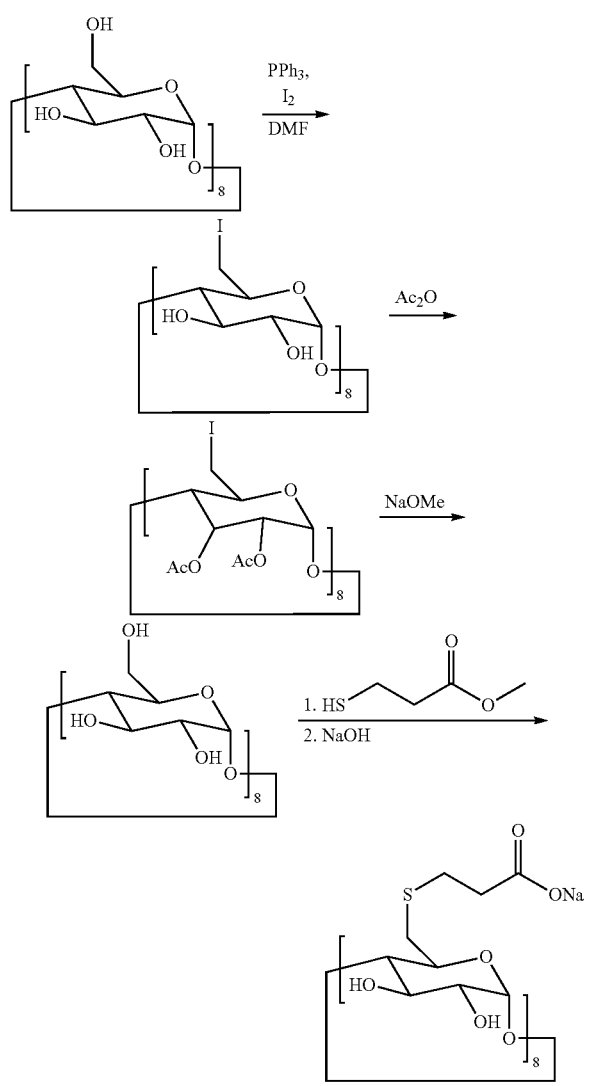

Patent application WO0140316PP disclosed that iodine, used as halogenating reagent, reacted with γ-cyclodextrin under the catalysis of triphenylphosphine to form 6-deoxy-6-periodo-γ-cyclodextrin; this intermediate further reacted with 3-mercaptopropionic acid to form a thioether, and the thioether was then purified by membrane dialysis to obtain the target product. This method is simple, reliable, and high-reactivity, but the purification of the product is only performed by membrane dialysis, therefore it is difficult to obtain high-purity sugammadex sodium.

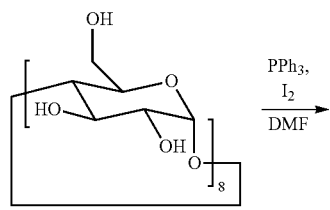

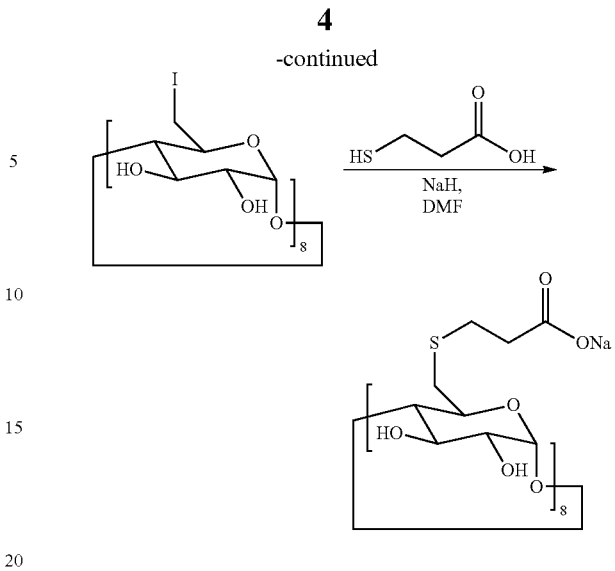

Patent application CN105348412 discloses a method for purifying crude sugammadex sodium. The crude sugammadex sodium was hydrolyzed under acidic conditions to obtain a free acid solid; the free acid solid was beaten, washed and purified with water; then the free acid was reacted with organic amine to prepare sugammadex ammonium salt; the obtained sugammadex ammonium salt was recrystallized for purification; the sugammadex ammonium salt was dissociated under acidic conditions to obtain free acid; the free acid solid was beaten, washed and purified; then the obtained free acid reacted with sodium hydroxide to obtain pure sugammadex sodium. In this method, column chromatography, dialysis or other purification methods were not used, but the steps are cumbersome, requiring multiple conversions between the free acid and the salt, and the operation is inconvenient. In addition, due to the instability of the sugammadex, the structure of the sugammadex has the risk of being dissociated during the dissociation process under acidic conditions, forming acid-destroying impurities and increasing the difficulty of purifying the product. This method also does not mention the protection of inert gas atmosphere, and has no condition for inhibiting the increase of the sugammadex oxidation impurities.

SUMMARY

The objective of the present invention is to overcome the drawbacks of the prior art and to provide a method for recrystallizing and purifying sugammadex sodium to obtain a product possessing less impurities and good stability.

The objective of the present invention is achieved by the following technical solutions: A method for refining sugammadex sodium: adding a protective agent to crude sugammadex sodium, and obtaining pure sugammadex sodium by performing recrystallization under the protection of inert gas; wherein, the protective agent is one or a mixture of two or more, in any ratio, selected from the group consisting of mercaptoethanol, thioglycolate, thioglycolate ester, mercaptopropionate, mercaptopropionate ester, glutathione, cysteine, cystamine, dithioerythritol, dithiothreitol, trisubstituted organophosphorus compound, and salt of the trisubstituted organophosphorus compound.

In the above-mentioned method for refining the sugammadex sodium, preferably, the mass ratio of the protective agent, to be added, to the crude sugammadex sodium is larger than or equal to 0.001%, and is more preferably ranging from 0.1% to 20%.

In the above-mentioned method for refining the sugammadex sodium, preferably, a solvent used for recrystallization is selected from the combination of good solvent water and the poor solvent of the sugammadex sodium; wherein, the poor solvent of the sugammadex sodium is one or a mixture of more selected from the group consisting of methanol, ethanol, acetonitrile, acetone, and N, N-dimethylformamide.

In the above-mentioned method for refining the sugammadex sodium, the trisubstituted organophosphorus compound is an organophosphorus compound bearing reducibility, which is composed of three identical or different substituent side chains bound to a phosphorus atom, using the phosphorus atom as the center atom. Preferably, the trisubstituted organophosphorus compound is one selected from the group consisting of triphenylphosphine (TPP), triethylphosphine (TEP), tris (2-carboxyethyl) phosphorus (TECP), and tris (2-furyl) phosphorus (TFP), or is one of the hydrochloride, sulfate, nitrate and phosphate of the above-mentioned compounds.

In the above-mentioned method for refining the sugammadex sodium, the specific process of recrystallization is as follows: dissolving the crude sugammadex sodium in water, adding a protective agent; under the protection of inert gas, heating the solution to reflux, and adding the poor solvent of the sugammadex sodium; and after the addition, cooling to −20° C. to 30° C. with stirring.

In the above-mentioned method for refining the sugammadex sodium, preferably, the inert gas is one selected from the group consisting of nitrogen, argon, helium, and carbon dioxide.

Beneficial Effects:

1. In the process of refining sugammadex sodium by recrystallization, by the action of the protective agent, the polymeric impurities having disulfide structures are removed from the crude sugammadex sodium, and at the same time, the formation of impurities such as sulfoxide and sulfone, etc. are inhibited, thus the purity of the sugammadex sodium product is improved.

2. By using the method of the present invention to refine the crude sugammadex sodium, the impurities can be removed effectively, the purity of the product is above 99.0%, the single impurity is less than 0.1%, the quality of the product met the quality requirements of the raw materials of injection, and met the relevant technical requirements of the Technical Guidelines ICH for EU Quality Studies, which provides qualified raw materials for the production of sugammadex sodium injection.

3. The refining method of the present invention has the advantages of simple process, low cost, easy operation, good economy, and is more suitable for industrial production; and the preparation prepared by using the raw material has the advantages of fewer impurities, good curative effect and low adverse reaction, which brings the greatest benefit to the patient.

DETAILED DESCRIPTION OF THE EMBODIMENTS

The preferred embodiments of the present invention will be further described in detail below. It should be understood that the methods described in the embodiments of the present invention are merely used to further illustrate the present invention, and are not intended to limit the present invention. Therefore, the simple improvements of the present invention derived based on the methods of the present invention should be included in the protective scope of the present invention.

The reagents, instruments and equipment used in the present invention are all commercially available unless otherwise stated herein.

Method for determining the purity by HPLC method is as follows. The sample to be tested is taken and placed in a 25 mL volumetric flask, a small amount of water is added and the volumetric flask is subjected to shaking to dissolve the sample, solvent is added to dilute the solution to the scale mark, and well shaking is performed to obtain the test solution. 1 mL of the test solution is precisely measured and placed in a 100 mL volumetric flask, solvent is added to dilute the solution to the scale mark, and well shaking is performed to obtain the control solution. According to the chromatographic conditions (octadecylsilane chemically bonded silica is used as a filler, phosphate buffer is used as mobile phase A, acetonitrile is used as mobile phase B, linear gradient elution is performed, detection wavelength is 200 nm) under the content determination item, 20 µl of control solution is taken and injected into the liquid chromatograph to adjust the sensitivity of the detector, so that the peak height of the chromatographic peak of the principal component is 10% to 25% of the full scale; then, 20 µl of test solution and 20 µl of control solution are accurately measured and injected into the liquid chromatograph, respectively; and the chromatogram is recorded as long as 3 times the retention time of the principal component peak. The sum of the peak area percentage of 6-octa-(2-carboxyethyl) thio-γ-cyclodextrin sodium salt and the peak area percentage of 6-hepta-(2-carboxyethyl) thio-γ-cyclodextrin sodium salt is the purity of the sample to be tested.

The crude sugammadex sodium is produced by the method disclosed in the patent application U.S. Pat. No. 6,670,340.

According to description in the published literature of the original research and development manufacturer, the pharmaceutically active ingredients of the sugammadex sodium product are mainly 6-octa-(2-carboxyethyl) thio-γ-cyclodextrin sodium salt and 6-hepta-(2-carboxyethyl) thio-γ-cyclodextrin sodium salt. Therefore, the purity described in the following embodiments is the percentage of the sum of the masses of the 6-octa-(2-carboxyethyl) thio-γ-cyclodextrin sodium salt and the 6-hepta-(2-carboxyethyl) thio-γ-cyclodextrin sodium salt in the product to the mass of the product.

Figure 1:
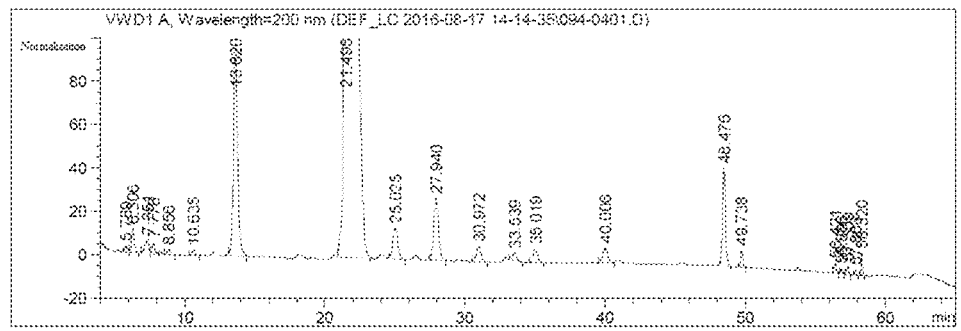
FIG. 1 is an HPLC spectrogram of crude sugammadex sodium.

Reference Embodiment: Preparation of Crude Sugammadex Sodium 3-mercaptopropionic acid (12.2 mL, 140 mol) is added to the reaction flask, 450 mL of N, N-dimethylformamide is added, and sodium hydride (12.3 g, 308 mol, 60%) is added in three batches under the protection of nitrogen atmosphere at room temperature. After the addition, the mixture is stirred at room temperature for 30 min, and γ-iodo-cyclodextrin (31.2 g, 14 mmol, dissolved in 450 mL of N,N-dimethylformamide) is added dropwise, and after the addition, the mixture is heated to 70° C. to react for 12 h. After the reaction, the mixture is cooled to room temperature, 100 mL of water is added, stirred, and the mixture is subjected to a reduced pressure distillation until 400 mL of the solvent remains. Then, 2 L of ethanol is added, the mixture is filtered, and the solids are collected and dried under vacuum to obtain 45 g of pale-yellow solids with a purity of 91.92%. The test results of the crude sugammadex sodium are shown in FIG. 1.

Figure 2:
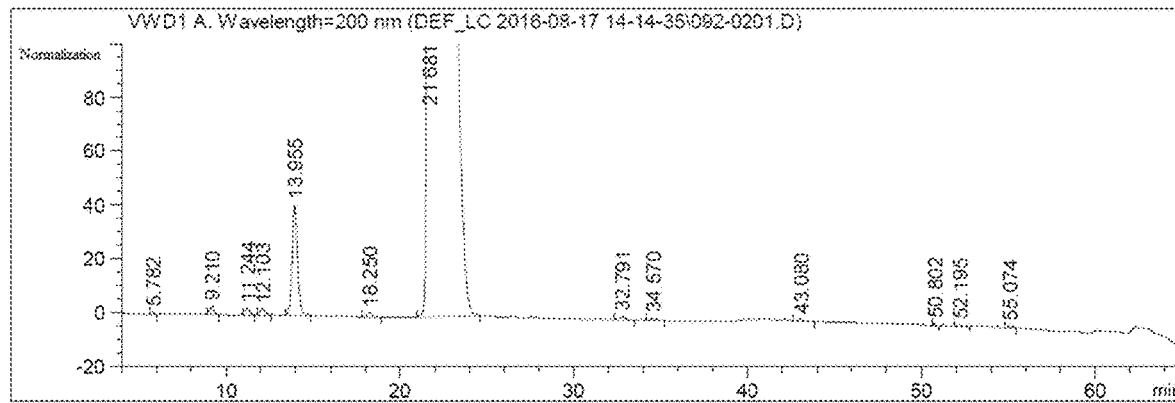
FIG. 2 is an HPLC spectrogram of pure sugammadex sodium prepared by the method of the present invention.

Embodiment 1: Refining of Sugammadex Sodium 100 g of crude sugammadex sodium is taken and completely dissolved with 3 L of water, 3 g of glutathione is added under stirring; under the protection of nitrogen, the solution is heated to reflux, then 8 L of acetonitrile is added to the solution; after the addition, the solution is cooled to room temperature with stirring, and a large amount of white solids are precipitated out; after the filtration of the precipitated white solid, 33 g of pure sugammadex sodium with a purity of 99.56% is obtained, as shown in FIG. 2.

Embodiment 2: Refining of Sugammadex Sodium 100 g of crude sugammadex sodium is taken and completely dissolved with 3 L of water, 3 g of cysteine is added under stirring; under the protection of nitrogen, the solution is heated to reflux, then 8 L of acetonitrile is added to the solution; after the addition, the solution is cooled to room temperature with stirring, and a large amount of white solids are precipitated out; after the filtration of the precipitated white solid, 35 g of pure sugammadex sodium with a purity of 99.3% is obtained.

Embodiment 3: Refining of Sugammadex Sodium 100 g of crude sugammadex sodium is taken and completely dissolved with 3 L of water, 3 g of mercaptoethanol is added under stirring; under the protection of nitrogen, the solution is heated to reflux, then 8 L of acetonitrile is added to the solution; after the addition, the solution is cooled to room temperature with stirring, and a large amount of white solids are precipitated out; after the filtration of the precipitated white solid, 28 g of pure sugammadex sodium with a purity of 99.2% is obtained.

Embodiment 4: Refining of Sugammadex Sodium 100 g of crude sugammadex sodium is taken and completely dissolved with 3 L of water, 3 g of dithioerythritol is added under stirring; under the protection of nitrogen, the solution is heated to reflux, then 8 L of acetonitrile is added to the solution; after the addition, the solution is cooled to room temperature with stirring, and a large amount of white solids are precipitated out; after the filtration of the precipitated white solid, 32 g of pure sugammadex sodium with a purity of 99.3% is obtained.

Embodiment 5: Refining of Sugammadex Sodium 100 g of crude sugammadex sodium is taken and completely dissolved with 3 L of water, 5 g of triphenylphosphine is added under stirring; under the protection of nitrogen, the solution is heated to reflux, then 8 L of acetonitrile is added to the solution; after the addition, the solution is cooled to room temperature with stirring, and a large amount of white solids are precipitated out; after the filtration of the precipitated white solid, 31 g of pure sugammadex sodium with a purity of 99.1% is obtained.

Embodiment 6: Refining of Sugammadex Sodium 100 g of crude sugammadex sodium is taken and completely dissolved with 3 L of water, 5 g of tris (2-carboxyethyl) phosphorus hydrochloride is added under stirring; under the protection of nitrogen, the solution is heated to reflux, then 8 L of acetonitrile is added to the solution; after the addition, the solution is cooled to room temperature with stirring, and a large amount of white solids are precipitated out; after the filtration of the precipitated white solid, 34 g of pure sugammadex sodium with a purity of 99.5% is obtained.

Embodiment 7: Refining of Sugammadex Sodium 100 g of crude sugammadex sodium is taken and completely dissolved with 3 L of water, 1 mg of glutathione is added under stirring; under the protection of nitrogen, the solution is heated to reflux, then 8 L of N, N-dimethylformamide is added to the solution; after the addition, the solution is cooled to room temperature with stirring, and a large amount of white solids are precipitated out; after the filtration of the precipitated white solid, 36 g of pure sugammadex sodium with a purity of 99.4% is obtained.

Embodiment 8: Refining of Sugammadex Sodium 100 g of crude sugammadex sodium is taken and completely dissolved with 3 L of water, 0.1 g of glutathione is added under stirring; under the protection of nitrogen, the solution is heated to reflux, then 8 L of N, N-dimethylformamide is added to the solution; after the addition, the solution is cooled to room temperature with stirring, and a large amount of white solids are precipitated out; after the filtration of the precipitated white solid, 35 g of pure sugammadex sodium with a purity of 99.5% is obtained.

Embodiment 9: Refining of Sugammadex Sodium 100 g of crude sugammadex sodium is taken and completely dissolved with 3 L of water, 20 g of glutathione is added under stirring; under the protection of nitrogen, the solution is heated to reflux, then 8 L of N, N-dimethylformamide is added to the solution; after the addition, the solution is cooled to room temperature with stirring, and a large amount of white solids are precipitated out; after the filtration of the precipitated white solid, 27 g of pure sugammadex sodium with a purity of 99.6% is obtained.

Comparative Example 1

Figure 3:
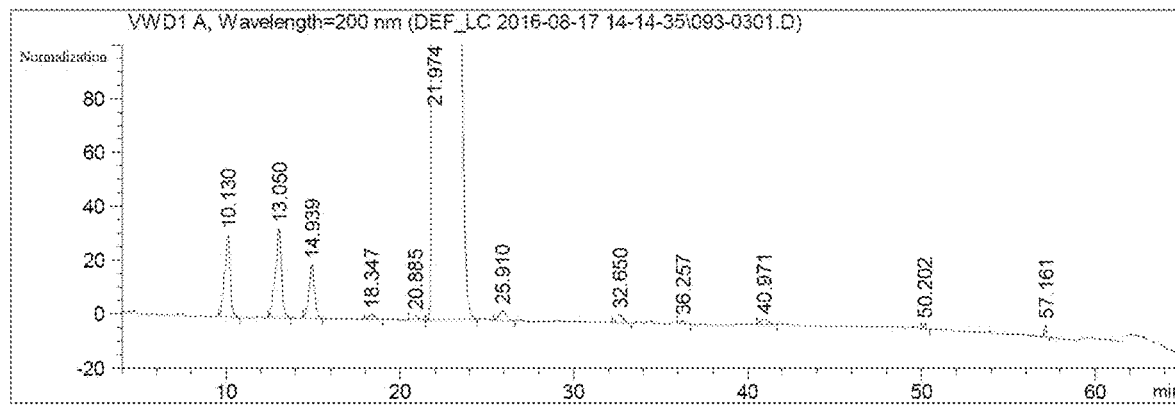
FIG. 3 is an HPLC spectrogram of pure sugammadex sodium prepared by a recrystallization under a protection of displacing oxygen with inert gas.

100 g of crude sugammadex sodium is taken and completely dissolved with 3 L of water; under conditions of strictly controlled oxygen-free and the protection by multiple displacement of inert gas, the solution is heated to reflux, then 8 L of acetonitrile is added to the solution; after the addition, the solution is cooled to room temperature with stirring, and a large amount of white solids are precipitated out; after the filtration of the precipitated white solid, 32 g of fine sugammadex sodium with a purity of 97.84% is obtained, as shown in FIG. 3.

Since the thioether bond in the molecular structure of sugammadex sodium is extremely easy to be oxidized, the increase of oxidation impurities cannot be avoided simply by using inert gas protection method or other oxygen eliminating methods. Comparing Comparative Example 1 with Embodiments 1-9, it is known that under the premise of not adding the protective agent of the present invention, even under the conditions of strictly controlled oxygen-free and the protection by multiple displacement of inert gas, the increase of the oxidation impurities cannot be effectively controlled by the conventional recrystallization method, and at the same time, impurities such as disulfide may not be removed to improve the purity of the product, and the refined product has poor purity.

In general, it is difficult to control a single impurity, such as sulfoxides, sulfones, and disulfide in the sugammadex sodium product, to be below 0.1% by a conventional recrystallization method. Moreover, the quality of the obtained product is difficult to meet the quality requirements of the raw materials of the injection, and is difficult to meet the relevant technical requirements of the Technical Guidelines ICH for EU Quality Studies; and the refining product has a relatively low yield, high cost, which is difficult to industrialize.

Comparative Example 2

Figure 4:
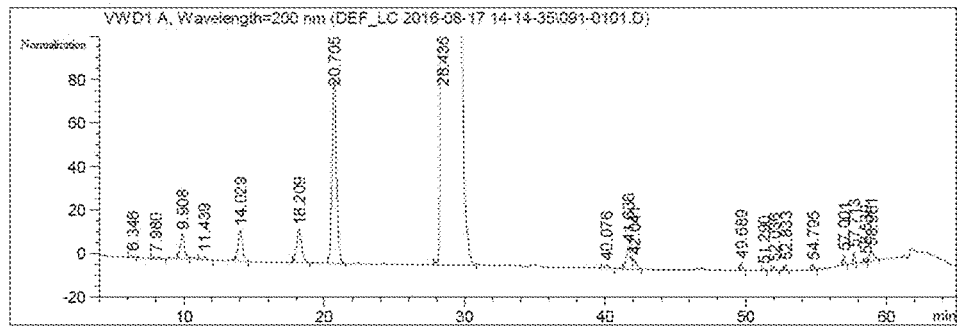
FIG. 4 is an HPLC spectrogram of a commercially available sugammadex sodium injection.

The test results of the commercially available sugammadex sodium injection showed that the purity was 97.77%, as shown in FIG. 4.

It can be seen from the comparison between Comparative Example 2 and Embodiments 1-9 that the purity of the sugammadex sodium obtained by the present invention is higher than that of the commercially available product.

The foregoing descriptions are merely preferred embodiments of the present invention, which are not used to limit the present invention. Any modifications, equivalent substitutions, improvements within the spirit and principle of the present invention should be included in the protective scope of the present invention.

What is claimed is:

1. A method for refining sugammadex sodium, comprising the following steps: adding a protective agent to crude sugammadex sodium, and obtaining pure sugammadex sodium by performing recrystallization under the protection of inert gas; wherein the protective agent is one or a mixture of two or more selected from the group consisting of mercaptoethanol, thioglycolate, thioglycolate ester, mercaptopropionate, mercaptopropionate ester, glutathione, cysteine, cystamine, dithioerythritol, dithiothreitol, trisubstituted organophosphorus compound, and salt of the trisubstituted organophosphorus compound.

2. The method according to claim 1, wherein a mass ratio of the protective agent, to be added, to the crude sugammadex sodium is larger than or equal to 0.001%.

3. The method according to claim 2, wherein the mass ratio of the protective agent, to be added, to the crude sugammadex sodium is ranging from 0.1% to 20%.

4. The method according to claim 1, wherein a solvent used for the recrystallization is selected from a combination of water and a poor solvent of the sugammadex sodium; and wherein the poor solvent of the sugammadex sodium is one or a mixture of more selected from the group consisting of methanol, ethanol, acetonitrile, acetone, and N, N-dimethylformamide.

5. The method according to claim 1, wherein the trisubstituted organophosphorus compound is one selected from the group consisting of triphenylphosphine (TPP), triethylphosphine (TEP), tris (2-carboxyethyl) phosphorus (TCEP), and tris (2-furyl) phosphorus (TFP), or is one of hydrochloride, sulfate, nitrate and phosphate of the riphenylphosphine (TPP), the triethylphosphine (TEP), the tris (2-carboxyethyl) phosphorus (TCEP), and the tris (2-furyl) phosphorus (TFP).

* * * * *